United States Patent [19]

Dea et al.

[11] 4,147,769
[45] Apr. 3, 1979

[54] MICROBICIDAL COMPOSITION

[75] Inventors: Frank J. Dea, Newport Beach; William D. Fairbairn, Atherton; Michael W. Novack, San Juan Capistrano, all of Calif.

[73] Assignee: Nelson Research & Development Company, Irvine, Calif.

[21] Appl. No.: 867,805

[22] Filed: Jan. 9, 1978

Related U.S. Application Data

[63] Continuation of Ser. No. 700,311, Jun. 28, 1976, abandoned, which is a continuation-in-part of Ser. No. 489,708, Jul. 18, 1974, abandoned.

[51] Int. Cl.$^2$ .......................... A61K 7/00; A61L 9/04
[52] U.S. Cl. ......................................... 424/47; 424/45
[58] Field of Search .............................. 424/45, 46, 47

[56] References Cited

U.S. PATENT DOCUMENTS

| | | | |
|---|---|---|---|
| 3,065,139 | 11/1962 | Ericsson et al. | 424/141 |
| 3,472,928 | 11/1969 | Virzi | 424/47 X |
| 3,480,185 | 11/1969 | Steinberg et al. | 424/45 |
| 3,574,821 | 4/1971 | Pfirrmann et al. | 424/55 |
| 3,681,492 | 8/1972 | Kotzbauer | 424/141 |

OTHER PUBLICATIONS

Abstract of S. Africa App. 69/8513, 7/70.

*Primary Examiner*—Frederick E. Waddell
*Attorney, Agent, or Firm*—Martin A. Voet

[57] ABSTRACT

There is disclosed a shelf-stable microbicidal composition containing no water and including an ene-diol compound, a specific catalytic metal compound, and a propellant suitable for dispensing the ingredients from an aerosol container, with at least one of the ene-diol compound and the catalytic metal compound not in solution. Oxidation of the ene-diol compound catalyzed by the metal compound produces a microbicidal effect.

2 Claims, No Drawings

MICROBICIDAL COMPOSITION

RELATION TO EARLIER FILED APPLICATION

This Application is a Continuation of Application Ser. No. 700,311 filed June 28, 1976, now abandoned, which in turn is a Continuation-in-part of Application Ser. No. 489,708, filed July 18, 1974, now abandoned.

BACKGROUND OF THE INVENTION

It is known that the relatively rapid oxidation of an ene-diol compound in the presence of catalytic metal ions, notably copper ions, effects substantially a complete kill of microorganisms which are in contact with it, e.g. U.S. Pat. No. 3,065,139.

Commercial utility of the rapid oxidation of an ene-diol compound to obtain the benefit of its microbicidal effect is difficult because the reaction takes place so quickly when the necessary ingredients are in contact with each other that commercially packaged products do not have useful shelf life. U.S. Pat. No. 3,681,492 deals with aqueous compositions in which the rate of oxidation of ene-diols is retarded so that the microbicidal effects is sustained for a longer period. However, these compositions are not useful as commercial products because the reaction can only be retarded for a relatively short time, for example a matter of days, which is not long enough to provide a suitable shelf life for a commercial product. In addition, a highly retarded reaction is not as intense as an unretarded or a mildly retarded reaction so that the microbicidal effect is not as strong.

In the specification, the term microbe and variations of the word microbe are defined to include all microorganisms including, but not limited to, bacteria, fungi, and viruses.

THE INVENTION

This invention is an article of manufacture which overcomes the difficulties of making the microbicidal effects of the ene-diol oxidation reaction commercially available. The invention is an aerosol composition containing no water and including an ene-diol compound, a specific catalytic metal compound and a propellant. It is critical that at least one of the compounds not be in solution with the other compound, for the reason that when both compounds are dissolved and in mutual contact, the oxidation of the ene-diol occurs. it is preferred that the ene-diol be suspended in the propellant as a fine powder and that the much smaller quantity of the metal catalyst compound be dissolved in a suitable dispersant so that even distribution of the smaller amount of the catalyst can be easily effected.

Water must be excluded because it may dissolve both the ene-diol compound and the metal catalyst compound and causes immediate oxidation of the ene-diol compound. We have discovered that even water of crystallization must be excluded.

The composition of this invention includes a propellant and it therefore must be suitably packaged in an aerosol container. The composition so packaged has indefinite shelf life, and the one-diol compound is available to react when the composition is applied by being discharged from the container. Sufficient water is present from the surface of a human or animal body to solubilize the ene-diol and the catalytic metal compound and to start the oxidation reaction of the ene-diol compound almost immediately. The oxidation reaction produces more water which thereby increases the reaction rate. Atmospheric moisture also aids in starting the reaction.

The composition of this invention may contain additional ingredients to improve its usefulness for different specific purposes. Among the useful purposes for the composition of this invention is its use as a disinfectant for first aid kits or hospital emergency or operating rooms. The composition packaged as an aerosol spray can be sprayed directly into wounds and the surrounding area, thereby killing substantially 100% of the microbes on the wound surface and on the skin area surrounding it. The composition may also be used to maintain sterile conditions in surgery, for example by spraying a surgeon's hands after scrubbing and by spraying the skin of a patient prior to incision.

If a sustained microbicidal effect is desired, some weakly metal-complexing agents, such as a nitrogen-containing inhibitor can be included in the composition to retard the rate of reaction to the degree desired. The preferred nitrogen-containing inhibitor is ammonium chloride. Other nitrogen retarding agents are disclosed in U.S. Pat. No. 3,681,492 and are incorporated herein by this reference. Other ingredients useful for a microbicidal composition may be inactive ingredients added to adjust to pH of the composition or adjuvants such as benzocaine, butacaine, butylaminobenzoate, eugenol, etc., which are commonly employed to anesthetize the area sprayed to reduce wound pain.

Another use for the composition of the present invention is in deodorant and deoderant/antiperspirant compositions. The microbicidal effect of the composition of this invention provides a significant deodorant effect. When used as a deodorant/antiperspirant, the composition may contain conventional antiperspirants, such as, for example, zirconium salts, as disclosed in U.S. Pat. Nos. 2,814,584 and 2,814,585, aluminum chloride or aluminum chlorhydrate as a suitable astringent antiperspirant. The preferred antiperspirant is aluminum chlorhydrate. When antiperspirant is employed in the composition of this invention, it is preferably present in an amount of from about 1% to about 15% on a weight basis. It is also preferred that deodorant compositions include known inhibitors to prolong the microbicidal effect for a suitable period of time, for example 24–48 hours.

Another use for compositions of this invention is in microbicidal and deodorant sprays applied to the inguinal areas of human bodies or to external genital organs. These compositions preferably contain a fragrance and metal-complexing agent to reduce the rate of the oxidation reaction in addition to the ene-diol compound, the metal catalyst compound, and the propellant. A suitable astringent may also be included.

Compositions employed on the skin of human beings may contain an emollient to soothe the skin of a user and to hold particles of powdered ene-diol compound and catalyst in contact with the skin in that most emollients are viscous and oily. A preferred emollient is isopropyl myristate.

For cosmetic purposes the composition may include such ingredients as fragrances and fine powders. For combating athletes foot, a spray may contain talc or non-wettable starch so that the area treated is provided with a soothing and drying residue; and adjuvants such as zinc oxide, zinc undecylanate, or undecylenic acid may also be incorporated in the compositions to provide their usual functions. It is evident that the composition of this invention may include other ingredients to adapt it particularly to the surfaces to which it is to be applied for its microbicidal effect.

The ene-diol compound is any non-toxic, water soluble compound having two hydroxyl groups on adjacent carbon atoms which are connected with an ethylenic double bond. Typical ene-diol compounds are ascorbic acid, reductic acid, squaric acid, dihydroxymaleic acid, and dihydroxyfumaric acid, and their non-toxic salts and esters. Typical ene-diol compounds are ascorbic acid compounds which include the various forms of ascorbic acid itself, such as isoascorbic acid, salts of ascorbic acid such as sodium and potassium ascorbate, ascorbic acid esters such as ascorbyl palmitate, and derivatives that retain the ene-diol molecular structure. The preferred ene-diol compound is dihydroxymaleic acid.

The catalytic metal which we have found to be useful in this invention is cupric oleate. We have found that cupric oleate may be ideally used in an aerosol container for the reason that cupric oleate has been found to be completely inert while in the aerosol environment and will not allow premature reaction with the selected ene-diol and especially with the preferred ene-diol, dihydroxymaleic acid.

The use of other metal catalysts as described in U.S. Pat. No. 3,065,139 may result in an unstable composition. Since the catalyst is present in such small amounts compared with other ingredients, it is preferred to distribute it uniformly throughout the mixture by dispersing it in a suitable inert organic liquid such as, for example, mineral spirits.

The main functions of the propellant are to maintain the active ingredients in the absence of water and to distribute the active ingredients to the area to which they are to be applied. The propellant should not react chemically with the ene-diol compound or the copper oleate catalyst. The propellant should be compatible with the surface to be sprayed; for example, if it is to be applied to the human skin, it should not be irritating or allergenic. The propellant should also have a suitable vapor pressure at room temperature to drive the ingredients from an aerosol can. Preferred propellants are the halocarbon compounds known as Freons, low boiling paraffin hydrocarbons and compressed inert gases.

The ene-diol compound should be present in an amount of from 0.01–10% by weight of the composition. Since the copper oleate is a catalytic agent, it may be present in much smaller concentrations but should be present in an amount of from about 0.0001% to about 1% of the composition.

If a nitrogen-containing inhibitor is employed, it may be present in any amount to provide a degree of retardation of the reaction desired. Generally, amounts up to 1.5% weight of the composition are sufficient to inhibit the reaction for any period desired. Although amines may be employed, the preferred inhibitors of the present invention are ammonium compounds because many amines are partially soluble in Freons. The preferred ammonium compound is ammonium chloride which is available, abundant, inexpensive, and compatible with the human body.

The ranges of compositions mentioned above are preferred. It is evident that the amount of volatile propellant used can vary widely without influencing the residue on the sprayed surface. Thus, if the weight of active ingredients were cut in half and twice as much of the total composition were applied, although there would be a waste of propellant, the same result could be obtained. Accordingly, the ranges set forth above represent conservative use of propellant without sacrificing reasonable operability of aerosol devices and without causing over-application of active ingredients from normal usage.

DETAILED DESCRIPTION OF THE INVENTION

The following examples illustrate the effectiveness of specific embodiments of this invention.

EXAMPLE I (A) A composition was prepared containing the ingredients shown below. The cupric oleate was dispersed in the mineral spirits prior to combining with the remaining ingredients. The mixture was placed in glass aerosol containers, and it was permitted to stand for three months. A chemical analysis of the composition confirmed that there was substantially no oxidation of the dihydroxymaleic acid.

| Ingredients | % Wt. |
|---|---|
| Dihydroxymaleic acid | 0.5 |
| Ammonium chloride | 0.05 |
| Isopropyl myristate | 3. |
| Cupric oleate | 0.03 |
| Mineral spirits | 0.02 |
| Propellant (Freon 12/114, ratio of 1:3) | 96.4 |

(b) The mixture was sprayed for two seconds (approximately 6grams of aerosol mixture) onto a moist surface populated with $8.8 \times 10^5$ S. aureus, After one minute of contact time, 100% of the bacteria were killed. Attempts to grow S. aureus on the sprayed surface five hours later failed, indicating that the mixture was still antimicrobially active. The mixture described is particularly suitable as a topical antiseptic spray, to sterilize skin prior to surgery, to sterilize a surgeon's hands prior to surgery, or for other similar uses.

EXAMPLE II

The composition of Example I was prepared additionally containing 4% aluminum chlorhydrate. Upon standing three months in transparent aerosol containers, chemical analysis revealed substantially no oxidation of dihydroxymaleic acid. When applied to the axillae of human subjects in controlled tests, it was effective as a deodorant and antiperspirant.

We claim:

1. An article of manufacture, comprising an aerosol container containing a stable composition intended for use as an antimicrobial composition and containing no water, said composition comprising, on a weight basis, the following ingredients in approximately the percent amounts as shown.

| Ingredient | % Wt. |
|---|---|
| Dihydroxymaleic acid | 0.5 |
| Ammonium chloride | 0.05 |
| Isopropyl myristate | 3. |
| Cupric oleate | 0.03 |
| Mineral spirits | 0.02 |
| Propellant | 96.4 |

2. An article of manufacture, comprising an aerosol container containing a stable composition intended for use as a deodorant/antiperspirant and containing no water, said composition comprising, on a weight basis, the following ingredients in approximately the percent amounts shown.

| Ingredient | % Wt. |
|---|---|
| Dihydroxymaleic acid | 0.5 |
| Ammonium chloride | 0.05 |
| Aluminum chlorhydrate | 4. |
| Isopropyl myristate | 3. |
| Cupric oleate | 0.03 |
| Mineral spirits | 0.02 |
| Propellant | 92.4 |

* * * * *